United States Patent
Lamps et al.

(10) Patent No.: US 11,382,610 B2
(45) Date of Patent: Jul. 12, 2022

(54) ABDOMINAL CLOSURE METHOD AND DEVICE VARIATIONS

(71) Applicant: Absolutions Med, Inc., Mountain View, CA (US)

(72) Inventors: Gregory Lamps, Smyrna, GA (US); Kourosh Kojouri, San Jose, CA (US); Daniel Jacobs, Mountain View, CA (US)

(73) Assignee: Absolutions Med, Inc., Mountain View, CA (US)

(*) Notice: Subject to any disclaimer, the term of this patent is extended or adjusted under 35 U.S.C. 154(b) by 217 days.

(21) Appl. No.: 16/582,965

(22) Filed: Sep. 25, 2019

(65) Prior Publication Data

US 2020/0107826 A1     Apr. 9, 2020

Related U.S. Application Data

(60) Provisional application No. 62/784,175, filed on Dec. 21, 2018, provisional application No. 62/775,500, filed on Dec. 5, 2018, provisional application No. 62/740,589, filed on Oct. 3, 2018.

(51) Int. Cl.
  *A61B 17/04*   (2006.01)
  *A61B 17/08*   (2006.01)
  *A61B 17/00*   (2006.01)

(52) U.S. Cl.
  CPC ...... *A61B 17/0401* (2013.01); *A61B 17/0057* (2013.01); *A61B 17/08* (2013.01); *A61B 2017/00637* (2013.01); *A61B 2017/00663* (2013.01)

(58) Field of Classification Search
  CPC ............... A61B 17/08; A61B 17/0401; A61B 2017/00637; A61B 2017/00792; A61B 2017/0403–0464
  See application file for complete search history.

(56) References Cited

U.S. PATENT DOCUMENTS

| | | |
|---|---|---|
| 363,538 A | 5/1887 | Penny |
| 3,698,395 A | 10/1972 | Hasson |
| 3,926,193 A | 12/1975 | Hasson |
| 3,986,493 A | 10/1976 | Hendren |
| 4,060,089 A | 11/1977 | Noiles |
| 4,430,998 A | 2/1984 | Harvey et al. |
| 4,539,990 A | 9/1985 | Stivala |

(Continued)

FOREIGN PATENT DOCUMENTS

| | | |
|---|---|---|
| CN | 204428091 | 7/2015 |
| CN | 106901789 | 6/2017 |

(Continued)

OTHER PUBLICATIONS

Fernandez, L., "Abdominal Closure," *Medscape*, https://emedicine.medscape.com/article/1961789-technique, Jun. 14, 2019.

(Continued)

*Primary Examiner* — Shaun L David
(74) *Attorney, Agent, or Firm* — Levine Bagade Han LLP

(57) ABSTRACT

Abdominal closure reinforcement methods and tissue anchoring devices for reducing the rate of abdominal wall closure dehiscence are described. The tissue anchors avoid a permanent footprint of foreign material and precluding materials spanning the interior layer of the abdominal closure where risk to visceral structures exists.

29 Claims, 7 Drawing Sheets

(56) References Cited

U.S. PATENT DOCUMENTS

| | | |
|---|---|---|
| 4,548,202 A | 10/1985 | Duncan |
| 4,610,250 A | 9/1986 | Green |
| 4,667,674 A | 5/1987 | Korthoff et al. |
| 4,805,617 A | 2/1989 | Bedi et al. |
| 4,950,284 A | 8/1990 | Green et al. |
| 5,234,462 A | 8/1993 | Pavletic |
| 5,258,012 A | 11/1993 | Luscombe et al. |
| 5,263,971 A | 11/1993 | Hirshowitz et al. |
| 5,293,881 A | 3/1994 | Green et al. |
| 5,358,510 A | 10/1994 | Luscombe et al. |
| 5,534,010 A | 7/1996 | Peterson |
| 5,662,649 A | 9/1997 | Huebner |
| 5,800,436 A | 9/1998 | Lerch |
| 5,916,224 A | 6/1999 | Esplin |
| 6,485,503 B2 | 11/2002 | Jacobs et al. |
| 6,645,226 B1 | 11/2003 | Jacobs et al. |
| 6,730,014 B2 | 5/2004 | Wilk |
| 6,893,452 B2 | 5/2005 | Jacobs |
| 6,991,643 B2 | 1/2006 | Saadat |
| 7,156,862 B2 | 1/2007 | Jacobs et al. |
| 7,172,615 B2 | 2/2007 | Morriss et al. |
| 7,238,188 B2 | 7/2007 | Nesper et al. |
| 7,361,185 B2 | 4/2008 | O'Malley et al. |
| 7,445,010 B2 | 11/2008 | Kugler et al. |
| 7,510,566 B2 | 3/2009 | Jacobs et al. |
| 7,972,347 B2 | 7/2011 | Garvin et al. |
| 8,114,101 B2 | 2/2012 | Criscuolo et al. |
| 8,323,313 B1 | 12/2012 | Belson et al. |
| 8,663,275 B2 | 3/2014 | O'Malley et al. |
| 8,764,778 B2 | 7/2014 | Yeretsian |
| 8,801,754 B2 | 8/2014 | Walshe |
| 8,915,942 B2 | 12/2014 | Zhang |
| 9,149,297 B2 | 10/2015 | Kirschman |
| 9,179,914 B2 | 11/2015 | Belson et al. |
| 9,198,689 B2 | 12/2015 | Dale et al. |
| 9,271,730 B2 | 3/2016 | Fleischmann |
| 9,414,840 B2 | 8/2016 | Fleischmann |
| 9,474,529 B2 | 10/2016 | Belson et al. |
| 9,486,217 B2 | 11/2016 | Moustafa |
| 9,554,799 B2 | 1/2017 | Belson et al. |
| 9,662,112 B2 | 5/2017 | Nash et al. |
| 9,693,776 B1 | 7/2017 | Moustafa |
| 10,010,710 B2 | 7/2018 | Belson et al. |
| 10,022,216 B2 | 7/2018 | Ricci et al. |
| 10,456,136 B2 | 10/2019 | Belson et al. |
| 11,071,547 B2 | 7/2021 | Jacobs et al. |
| 2004/0059358 A1 | 3/2004 | Kortenbach et al. |
| 2004/0138683 A1 | 7/2004 | Shelton et al. |
| 2004/0267309 A1 | 12/2004 | Garvin |
| 2005/0197699 A1 | 9/2005 | Jacobs et al. |
| 2006/0058842 A1 | 3/2006 | Wilke et al. |
| 2006/0074448 A1 | 4/2006 | Harrison et al. |
| 2006/0167482 A1 | 7/2006 | Swain et al. |
| 2006/0247637 A1 | 11/2006 | Colleran et al. |
| 2007/0123914 A1 | 5/2007 | Lizard et al. |
| 2008/0046008 A1 | 2/2008 | Smith et al. |
| 2008/0262540 A1 | 10/2008 | Bangera et al. |
| 2008/0262543 A1 | 10/2008 | Bangera et al. |
| 2009/0163937 A1 | 6/2009 | Kassab et al. |
| 2009/0234358 A1 | 9/2009 | Morales et al. |
| 2011/0092993 A1 | 4/2011 | Jacobs |
| 2012/0029539 A1 | 2/2012 | Dennis |
| 2012/0130374 A1 | 5/2012 | Bouduban et al. |
| 2012/0221044 A1 | 8/2012 | Archibald et al. |
| 2013/0197577 A1 | 8/2013 | Wolf et al. |
| 2013/0325046 A1 | 12/2013 | Terwiske et al. |
| 2014/0094830 A1 | 4/2014 | Sargeant et al. |
| 2014/0214078 A1 | 7/2014 | Moustafa |
| 2014/0316323 A1 | 10/2014 | Kanevsky et al. |
| 2016/0095591 A1 | 4/2016 | Smith et al. |
| 2016/0113650 A1 | 4/2016 | Lord et al. |
| 2016/0249924 A1 | 9/2016 | Belson et al. |
| 2016/0310140 A1 | 10/2016 | Belson et al. |
| 2017/0156847 A1 | 6/2017 | Ricci et al. |
| 2017/0290580 A1 | 10/2017 | Soltanian |
| 2017/0296161 A1 | 10/2017 | Marshall |
| 2017/0325935 A1 | 11/2017 | Fuller et al. |
| 2018/0036006 A1 | 2/2018 | De Rezende Neto |
| 2018/0078257 A1 | 3/2018 | Buttar |
| 2018/0214148 A1 | 8/2018 | Christiansen et al. |
| 2019/0038274 A1 | 2/2019 | Quintero et al. |
| 2019/0167260 A1 | 6/2019 | Levinson et al. |
| 2020/0078018 A1 | 3/2020 | Jacobs et al. |
| 2020/0323614 A1 | 10/2020 | Lamps et al. |
| 2021/0128151 A1 | 5/2021 | Jacobs et al. |
| 2021/0212685 A1 | 7/2021 | Lamps et al. |

FOREIGN PATENT DOCUMENTS

| | | |
|---|---|---|
| CN | 107822682 | 3/2018 |
| WO | WO 2017/000758 | 1/2017 |
| WO | WO 2018/031509 | 2/2018 |
| WO | WO 2018/069543 | 4/2018 |
| WO | WO 2020/055757 | 3/2020 |
| WO | WO 2020/072259 | 4/2020 |
| WO | WO 2020/210463 | 10/2020 |
| WO | WO 2021/146165 | 7/2021 |

OTHER PUBLICATIONS

Lorenz® Plating System LactoSorb® RapidFlap™ LS brochure, 4 pages, Oct. 1, 2008.

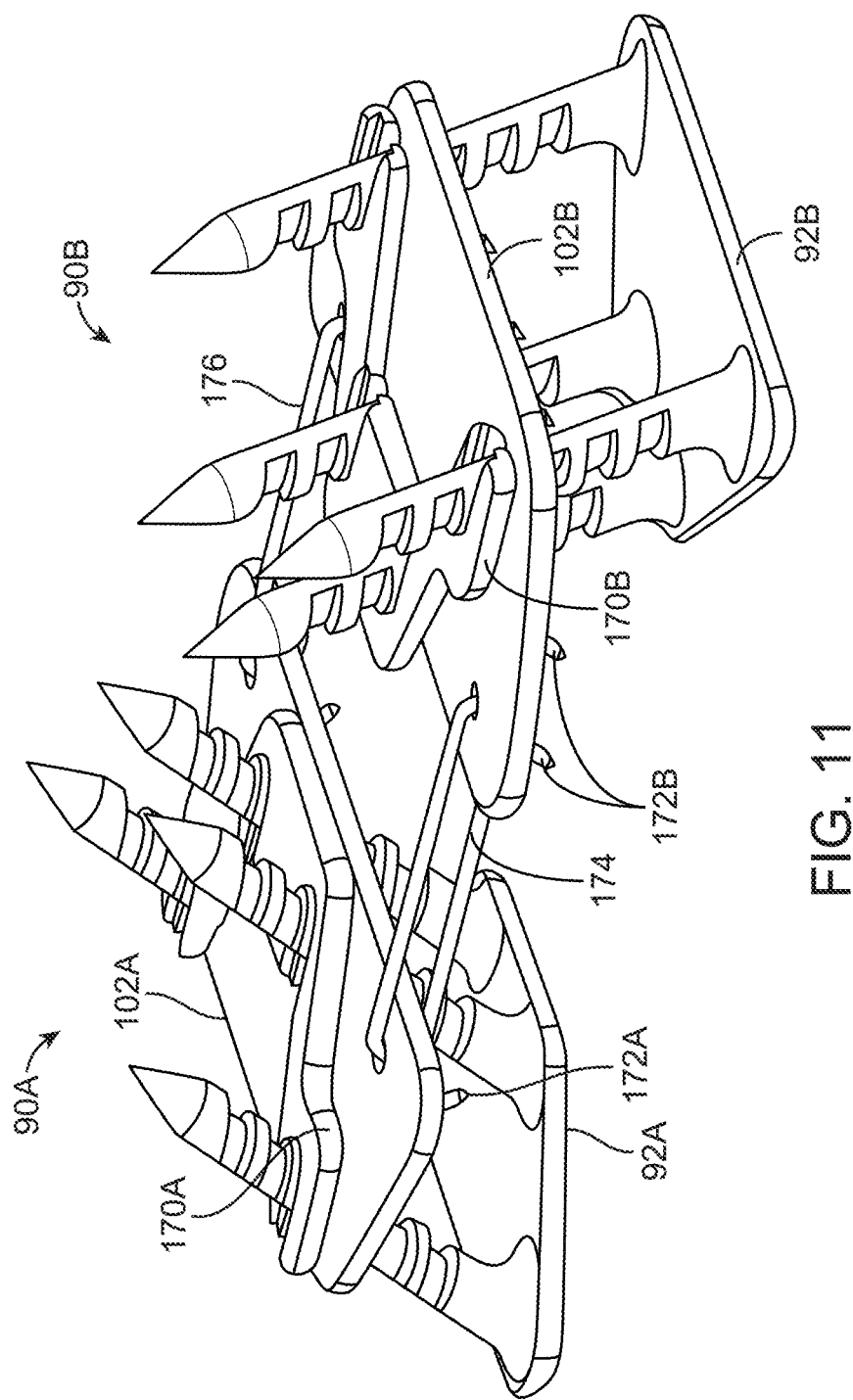

ABDOMINAL CLOSURE METHOD AND DEVICE VARIATIONS

CROSS-REFERENCE TO RELATED APPLICATIONS

This application claims the benefit of priority to U.S. Prov. App. 62/740,589 filed Oct. 3, 2018; 62/775,500 filed Dec. 5, 2018; and 62/784,175 filed Dec. 21, 2018, each of which is incorporated herein by reference in its entirety.

FIELD OF THE INVENTION

The present invention relates to methods and apparatus for distributing tension across an abdominal wall closure to aid healing and avoid dehiscence, while simultaneously protecting intra-abdominal viscera from device related injury.

BACKGROUND OF THE INVENTION

A ventral hernia occurs when there is a defect in the fascia and/or muscles of the anterior abdominal wall. Defects or comprised abdominal walls most commonly result from prior fascial incisions that did not adequately heal (incisional hernia), but also result from pregnancy, and de novo.

There are an estimated four million open abdominal surgeries in the United States and a commonly documented postoperative complication is incisional hernia, which occurs in up to 20% of patients after attempted abdominal closure. FIG. 1 shows an abdomen A of a patient illustrating common sites for ventral hernias, e.g., epigastric, abdominal, and incisional hernias.

Treatments for ventral hernias can fall into three typical categories: (1) spanning the defect with a prosthetic or biologic patch (e.g., mesh), (2) closing the defect under some tension and supporting the closure with a prosthetic or biologic patch, and (3) abdominal wall component separation in which a layer or layers of the muscles and fascia of the abdominal wall are divided in order to allow components to advance towards the midline such that the defect is closed with no abdominal wall gap—also usually supported by a patch. All techniques have profound drawbacks, many of which are associated with the use of a patch.

Mesh used to span abdominal wall defects or to support a fascial closure is a foreign body, fraught with all of the inherent risks that foreign bodies impose. The two most significant risks in this setting are infection and erosion into critical structures such as bowel. Both are devastating events. In the event of infection, whether acute or delayed, removing the mesh from the tissue that has grown into its interstices can be surgically traumatic if not impossible. Erosion into bowel not only sets infection into play, but additionally creates a life threatening or quality-of-life destroying loss of intestinal integrity, with intestinal contents leaking freely into the abdominal cavity, mesh, or through holes in the skin (enterocutaneous fistula). FIG. 2 shows an example of mesh 10 that has eroded into surrounding intestinal tissue.

An additional situation that abdominal surgeons often encounter is that of the difficult abdominal closure after trauma or extensive abdominal surgery. In such situations, swelling of the abdominal contents increases the intra-abdominal volume such that closure of the abdominal wall is either impossible or performed under excessively high tension. Soft tissues, however, cannot tolerate high tensions, and typically fail to remain opposed through healing, thus leading to a ventral hernia. Surgeons often use large retention sutures to hold the abdominal wall in position during the early post-operative phases in an attempt to prevent dehiscence (separation). Examples are shown in FIG. 3 which illustrates retention sutures with backing components 20 placed on both sides of the incision I and in FIG. 4 which illustrates retention sutures 30 directly across the midline of the incision I along the abdomen A.

Retention sutures 40, by design, typically have a segment running across the midline of the incisional closure both above and below (deep to) the abdominal wall AW, as shown in the schematic cross-sectional detail view of FIG. 5. The sutures 40 are placed such that a potential trapping space is defined between the suture 40 and the posterior abdominal wall; vector arrows 44 illustrate the net direction of force at the turning points of the suture 40 in the posterior fascia and skin. The segment below (deep to) the abdominal wall poses a threat to underlying bowel tissue. In addition, retention sutures 40, like most sutures, are relatively rigid and sharp, and can cut through tissue leading to incisional separation and failure of the repair. The length of suture placed against the skin surface may be enclosed in a tubular member 42 to prevent or inhibit erosion into the skin.

SUMMARY OF THE INVENTION

One approach to abdominal closure dehiscence is to maintain side-to-side apposition of the abdominal wall fascial edges while: (a) avoiding spanning materials deep to the abdominal wall (contradistinction to retention sutures) so as to preclude device related injury to the underlying intestine or organs; (b) avoiding permanent mesh or other material and their proclivity for complications, even years after surgery; (c) allowing easy placement of the tissue anchors; and (d) distributing tension across as many points and across the widest area practically allowed.

Generally, a soft tissue anchor that may extend entirely through a layer or layers of soft tissue and attach to opposing soft tissue may allow for the distribution of tensile forces across the soft tissues to approximate the edges of a wound or incision towards one another and/or to maintain approximated tissues against one another. The tissue anchor may be used in combination with sutures where the anchor and the sutures are both bioabsorbable leaving no permanent footprint of foreign material that can later lead to complications such as infection. Bioabsorbable materials may include, but are not limited to, polylactic acid (PLA), polyglycolic acid (PGA), lactic/glycolic acid copolymers (PLGA), polydiaxinone (PDO, PDS), polycaprolactone (PCL), etc.

In other variations, non-bioabsorbable materials may be used with the tissue anchor in various capacities. Such materials may include, but are not limited to, stainless steel, titanium, polyethylene (PE), polypropylene (PP), polyetheretherketone (PEEK), polyphenylene sulfide (PPS), or other materials which do not significantly degrade in the body over time.

In another variation, the tissue anchor may include a first tissue anchor having a distal anchor member coupled to a proximal anchor member via a connecting member. The distal anchor member may be configured to have one or more piercing elements such as tines which extend away from the platform of the distal anchor member such that they project towards the proximal anchor member. Similarly, the proximal anchor member may have one or more tines which extend away from the platform of the proximal anchor member such that they project towards the distal anchor member. The connecting member may be pivotably coupled to the distal anchor member and/or proximal anchor member such that the anchor members may pivot and angulate relative to one another and to the connecting member. Alternatively, one or both of the anchor members may be attached to the connecting member at a fixed angle to facilitate securement to the underlying tissue.

During use, the distal anchor member may be positioned against a tissue surface (e.g., along the abdominal wall) near or in proximity to a first edge of a wound or incision such that the one or more tines extend and penetrate posteriorly at least partially into the tissue such as the anterior rectus sheath, where medial abdominal wall tensile strength is greatest. The connecting member may extend entirely through the skin and/or the abdominal wall such that the proximal anchor member is positioned along opposite thickness of tissue, such as the posterior rectus sheath where present above the arcuate line. The one or more tines of the proximal tissue anchor may extend and penetrate anteriorly at least partially into the tissue such that the intervening tissue thickness is sandwiched between the first and second tissue anchors. For the purposes of discussion, proximal is used as a relative term as being closer to the core of the body and distal is used as a relative term as being further from the core of the body.

A second tissue anchor may be secured near or in proximity to a second edge of the wound or incision directly opposite, or in a staggered fashion opposite, to the first tissue anchor. Similarly, the second tissue anchor may have a distal anchor member having one or more tines which project at least partially into the underlying tissue and a proximal anchor member having one or more tines which project anteriorly at least partially into the underlying tissue. The distal and proximal anchor members may be coupled to one another via a connecting member which extends through the thickness of the secured tissue region.

With the tissue anchors secured to the first and second edges of the wound or incision, each of the distal anchor members may be coupled to one another via a connecting member such as a suture which may be secured to each of the tissue anchors, e.g., through one or more openings placed in the device to allow for suture passage. The suture from one tissue anchor can connect to a tissue anchor, e.g., on the contralateral side, such that the suture and tissue anchor assembly hold the edges in apposition while healing occurs.

Depending upon the length of the wound or incision, any number of pairs of tissue anchors may be applied to the tissue to approximate and/or maintain closure of the wound such that each of the tissue anchors are applied along the edges of the wound or incision adjacent to one another. The anchors may be placed in pairs directly opposite each other across the wound or incision or they may be staggered.

The connecting members that pass through the abdominal wall fascia and muscle may be angled or hinged relative to the respective anchor members to allow the medial forces of the suture to align more in parallel with the anchoring component. This may help to reduce an anterior moment arm that would tend to apply all or most of the force at the anterior rectus sheath rather than across the entire abdominal wall thickness (anterior rectus sheath, rectus muscle, posterior rectus sheath where present). Additionally, each of the components of the tissue anchors may be fabricated from fully bioabsorbable materials such that the tissue anchors may be left in place to bioabsorb into the body over time. Alternatively, portions of the tissue anchors, such as the posterior anchor members and/or connecting members may be bioabsorbable while the distal anchor members may be non-bioabsorbable. Once the wound or incision has healed and adhered sufficiently, the distal anchor members may be detached and removed from the tissue while the connecting members and proximal anchor members may be left in the body to become absorbed.

Another variation may include a first tissue anchor having a posterior anchor member with one or more tines extending in a distal direction at least partially into the overlying tissue. One or more columns each defining a lumen may project from the posterior anchor member so that when the anchor member is deployed against the tissue interior surface, each of the columns may extend through the full thickness of fascia and/or skin tissue. The posterior anchor member may have the one or more columns extend at an angle relative to the anchor member so that the columns emerge from the tissue at an angle.

With a second tissue anchor secured to a second edge of the wound or incision directly opposite to the first tissue anchor, a flexible couple member such as a suture may be passed through each of the columns through a respective opening and through the length of the tissue anchor to join each of the tissue anchors. The suture may be tightened to approximate and/or maintain the edges of the wound or incision towards or directly against one another. The second tissue anchor may likewise have a posterior anchor member with one or more tines projecting into the contacted tissue. The one or more columns may project from the anchor member with a suture passing between openings, through the columns, through or along each anchor member, back through columns, and through respective openings.

Yet another variation of the tissue anchor may comprise a first platform having one or more tines which each project from the platform. Each of the tines may extend in parallel with one another or one or several of the tines may angled differently from one another. A second platform may be separately attachable to each of the tines of the first platform at various levels or distances such that a tissue region, such as the tissue near or in proximity to an edge of a wound or incision, may be sandwiched or secured between the first and second platform.

The first platform may be formed in various configurations (e.g., circular, ovular, triangular, rectangular, rhomboid, etc.) although the variation may have a trapezoid-shaped configuration. The second platform may also have a similar or same shape as the first platform such that the first and second platforms may be oriented in the same direction. In other variations, the first and second platforms may each have a shape or configuration which is different from one another provided that the second platform is still connectable to the first platform.

The first edge may further define a slot or channel which is located along the edge corresponding to a position of the one or more tines extending from the first platform. Hence, a first slot may be defined along the first edge at a location corresponding to a first tine and a second slot may be defined along the first edge at a location corresponding to a second tine. A third slot may be defined along the first edge at a location corresponding to a third tine and a fourth slot may be similarly defined along the first edge at a location corresponding to a fourth tine. Each of the slots may correspond to the number of tines projecting from the first platform.

In use, the one or more tines of the first platform may be pierced into a tissue region (such as the interior of the abdominal wall) and advanced entirely through the tissue thickness (e.g., fascia and skin or at least penetrate through the anterior rectus sheath, where tissue tensile strength is greatest) until the tissue abuts against the first platform. The second platform may be positioned into proximity of the tines projecting through the tissue region and then slid to engage the first platform by advancing the tines into and through a corresponding slot. The second platform may be engaged with the first platform such that the two platforms are maintained in a parallel orientation relative to one another. Each of the tines may have predefined regions of reduced diameter over which the corresponding slots may selectively engage such that the parallel orientation between the platforms is maintained. The second platform may be advanced along the tines until the second platform is fully engaged to the tines at the terminal ends of the slots. The second platform may be positioned along the tines such that the second platform is positioned upon the tissue outer surface (such as the exterior of the abdominal wall or skin surface) and the tissue thickness is sandwiched or securely retained between each of the platforms. Any length of the tines protruding beyond the second platform may be cut, broken, or otherwise removed such that the tissue anchor maintains a low profile relative to the tissue surface.

The second tissue anchor may be secured in proximity to the edge of the wound or incision opposite to the first tissue anchor in the same manner, as described, such that the first and second tissue anchors may be attached or coupled to one another to approximate the tissue edges and maintained in apposition during healing. The tissue anchors may be secured, e.g., via lengths of spanning suture or other materials attached through openings defined along the second platform. In other variations, other spanning structures may be used in place of sutures, e.g., elastic member, springs, coils, ratcheted device, spanning screw, adjustable staple or fixed staple, or other structure that crosses from a first tissue anchor to a second tissue anchor to cause and hold apposition of the abdominal wall tissues. With the tines along each of the tissue anchors angled towards one another (or angled towards the wound or incision), any forces imparted upon the tissue due to the approximation of the tissue anchors towards one another may be mitigated by a reduction in the moment arm of the tines upon the tissue thickness due to the tines angle relative to the first platform.

Moreover, with the tissue anchor secured through the tissue thickness, the entire tissue anchor may be fabricated from a bioabsorbable material, as described herein, such that the tissue anchor may be left in place in the body after the tissue has healed leaving the anchor to degrade and absorb over time, thereby eliminating the need to remove the tissue anchor. Alternatively, the first platform and tines may be fabricated from a bioabsorbable material while the second platform may be fabricated from a non-bioabsorbable material, e.g., plastics, metals, alloys, etc. Once the tissue region has healed, the second platform may be detached from the tines and then removed from the body leaving the first platform and tines within the body to degrade and absorb.

Additionally and/or alternatively, the tissue anchors may be secured in the tissue by use in combination with an absorbable or permanent mesh or a biologic sheet or insert. The one or more tines may be pierced into and through the mesh which may be placed against the tissue surface. The mesh or biologic component may sit at any plane in the abdominal wall anatomy while fixated by the tissue anchor.

One variation of a tissue anchor apparatus may generally comprise a first platform defining one or more anchoring members having a length extending from a surface of the first platform, each of the one or more anchoring members having a terminal piercing end and defining one or more shoulders along the length, and a second platform defining one or more channels extending from an edge of the second platform. A position of the one or more channels along the edge may correspond to a position of the one or more anchoring members such that each of the one or more anchoring members is slidingly received along a respective channel while an orientation of the second platform relative to the first platform is maintained by the one or more shoulders.

One variation of a method for securing a tissue region may generally comprise piercing one or more anchoring members extending from a surface of a first platform through a thickness of a first tissue region which is in proximity to a wound or incision, and engaging a second platform to the one or more anchoring members of the first platform projecting beyond the thickness of the first tissue region by sliding each of the one or more anchoring members into and along a respective channel extending from an edge of the second platform while maintaining an orientation of the second platform relative to the first platform, wherein the thickness of the first tissue region is secured between the first platform and second platform.

Another variation of a tissue anchoring assembly may generally comprise a first platform having one or more piercing members projecting from a first surface and configured for contact against a first tissue region, and one or more first tubular members extending from the first surface and configured for placement through the first tissue region, the one or more first tubular members each defining a first opening. A second platform having one or more piercing elements may extend from a second surface configured for contact against a second tissue region, and one or more second tubular members extending from the second surface and configured for placement through the second tissue region, the one or more second tubular members each defining a second opening. Furthermore, one or more lengths of suture may extend between the first opening and the second opening such that the first platform and second platform are configured to cooperatively approximate the first tissue region and the second tissue region towards one another.

Another variation of a tissue anchor may generally comprise a first platform having one or more piercing elements extending from a first surface configured for contact against a first tissue surface, a tubular member extending from the first surface and configured for placement through the first tissue region, a distal end of the tubular member defining at least one opening, and a second platform having one or more piercing elements extending from a second surface configured for contact against a second tissue surface opposite to the first tissue surface.

Yet another variation of a tissue anchor may generally comprise a first platform having one or more piercing elements extending from a first surface configured for contact against a first tissue surface, and one or more tubular members extending from the first surface and configured for placement through the first tissue surface. Wherein the one or more tubular members may each define a lumen extending through such that each lumen of the one or more tubular members are in communication with one another via the first platform, and wherein a proximal end of the one or more tubular members may each define an opening in communication with a respective lumen.

BRIEF DESCRIPTION OF THE DRAWINGS

FIG. 11 illustrates another variation in which opposed suture anchors may each include a retainer member and a cap or securing member which may be attached to the tines along with one or more sutures (or other securement elements or biasing members) extending between the anchors.

DETAILED DESCRIPTION OF THE INVENTION

A soft tissue anchor that may extend entirely through a layer or layers of soft tissue and attach to opposing soft tissue may allow for the distribution of tensile forces across the soft tissues to approximate the edges of a wound or incision towards one another and/or to maintain approximated tissues against one another. In one embodiment, the tissue anchor may be used in combination with sutures where the anchor and the sutures are both bioabsorbable leaving no permanent footprint of foreign material that can later lead to complications such as infection. Bioabsorbable materials may include, but are not limited to, polylactic acid (PLA), polyglycolic acid (PGA), lactic/glycolic acid copolymers (PLGA), polydiaxinone (PDO, PDS), polycaprolactone (PCL), etc. Furthermore, any number of the tissue anchors may be deployed in an adjacent manner along the edges of the wound or incision to approximate pairs of tissue anchors towards one another on opposite edges of the wound or incision. Additionally, and/or alternatively, the tissue anchors may be deployed to maintain the edges of the wound or incision against one another until the wound or incision has healed.

In other variations, non-bioabsorbable materials may be used with the tissue anchor in various capacities. Such materials may include, but are not limited to, stainless steel, titanium, polyethylene (PE), polypropylene (PP), polyetheretherketone (PEEK), polyphenylene sulfide (PPS), or other materials which do not significantly degrade in the body over time.

Figure 1:
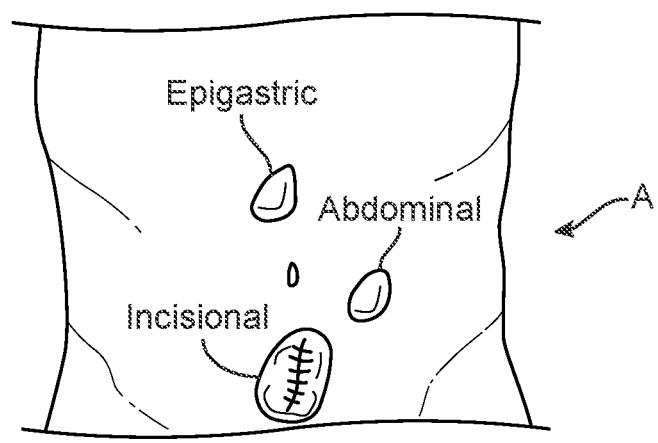
FIG. 1 an abdomen of a patient illustrating common sites for ventral hernias.
Figure 2:
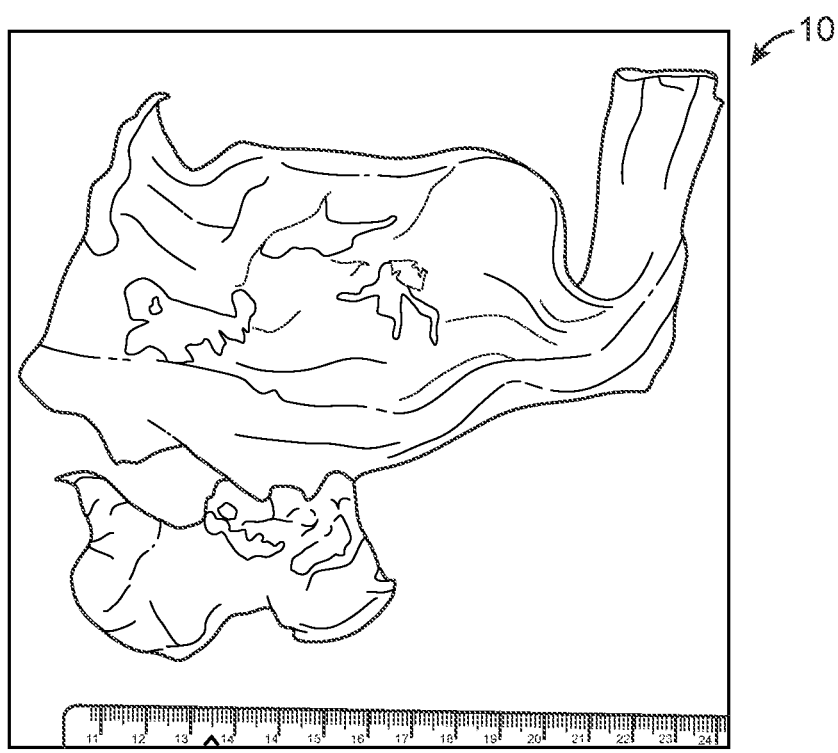
FIG. 2 shows an example of mesh that has eroded into intestinal tissue.
Figure 3:
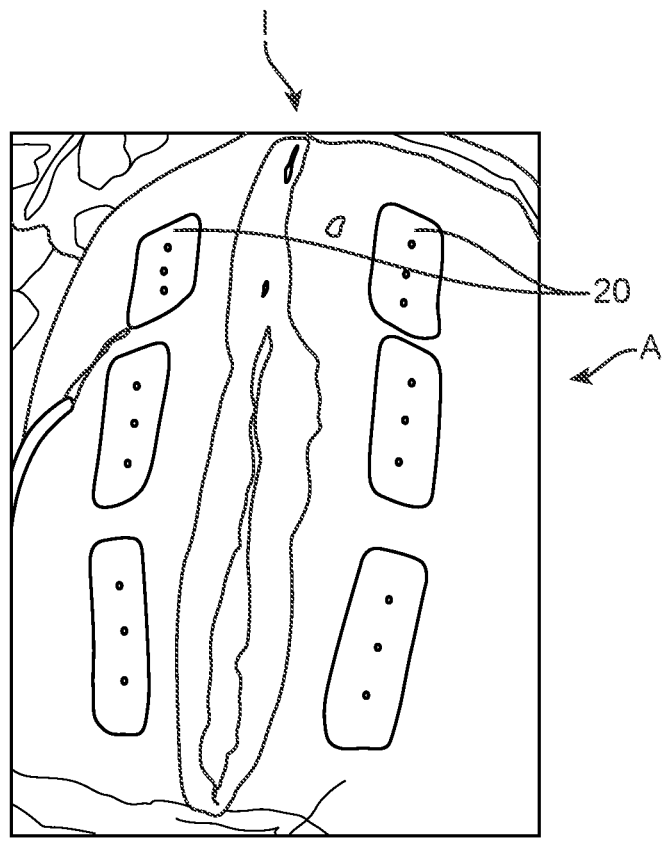
FIG. 3 shows an example of large sutures traversing the abdominal closure to hold tissue position during the early post-operative phases.
Figure 4:
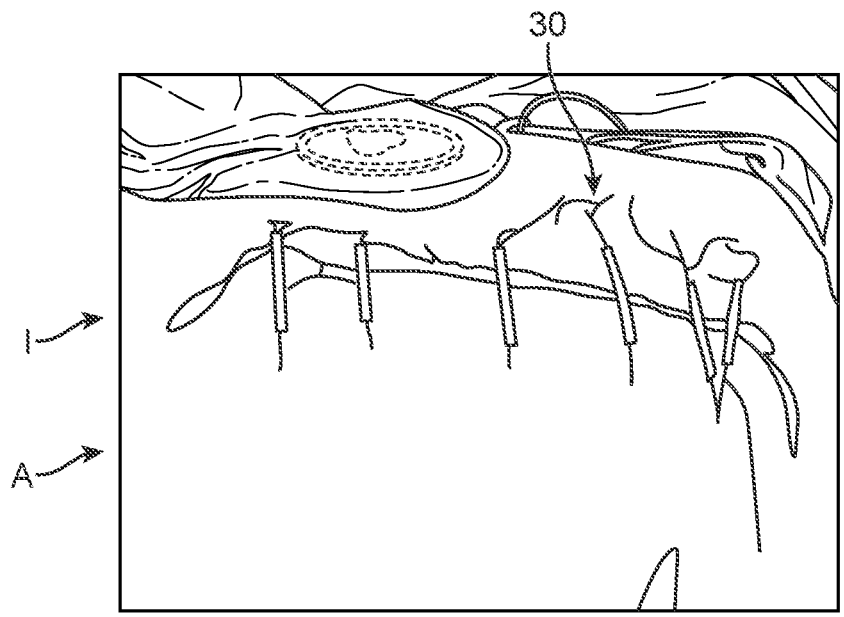
FIG. 4 shows retention sutures.
Figure 5:
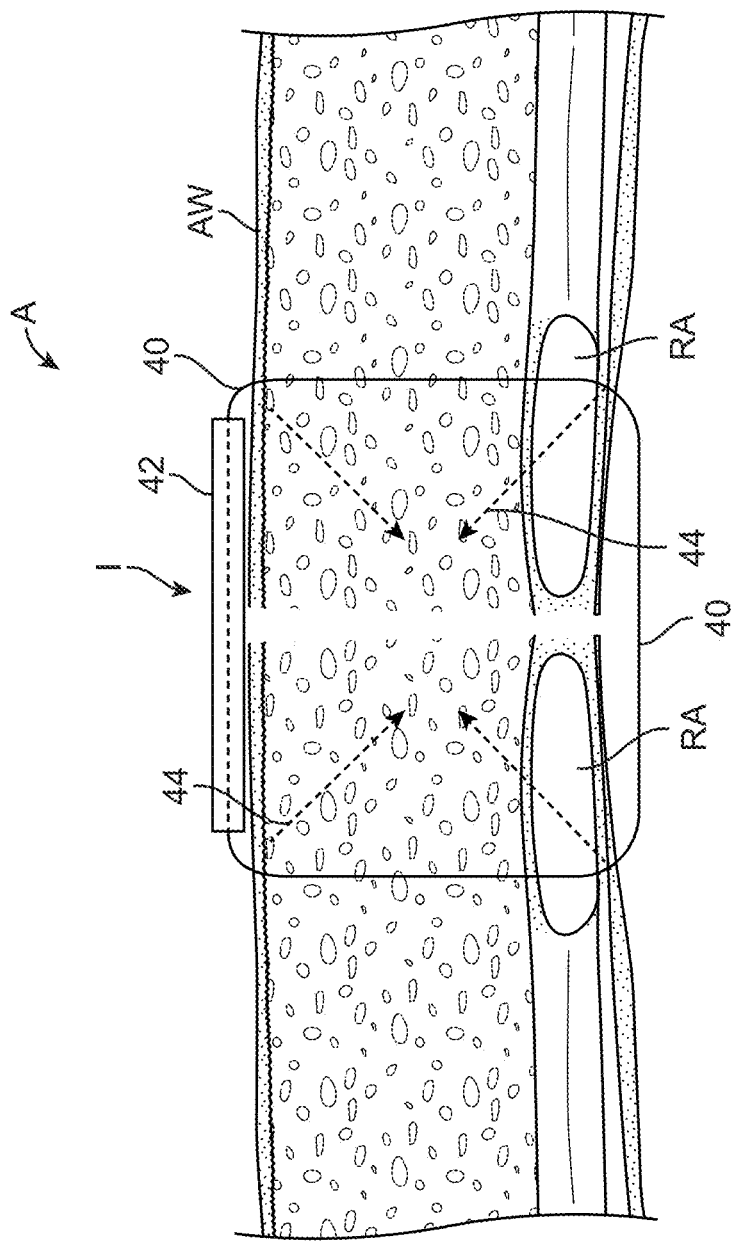
FIG. 5 shows an illustrative cross-sectional side view of a commonly used technique of placing retention sutures.
Figure 6:
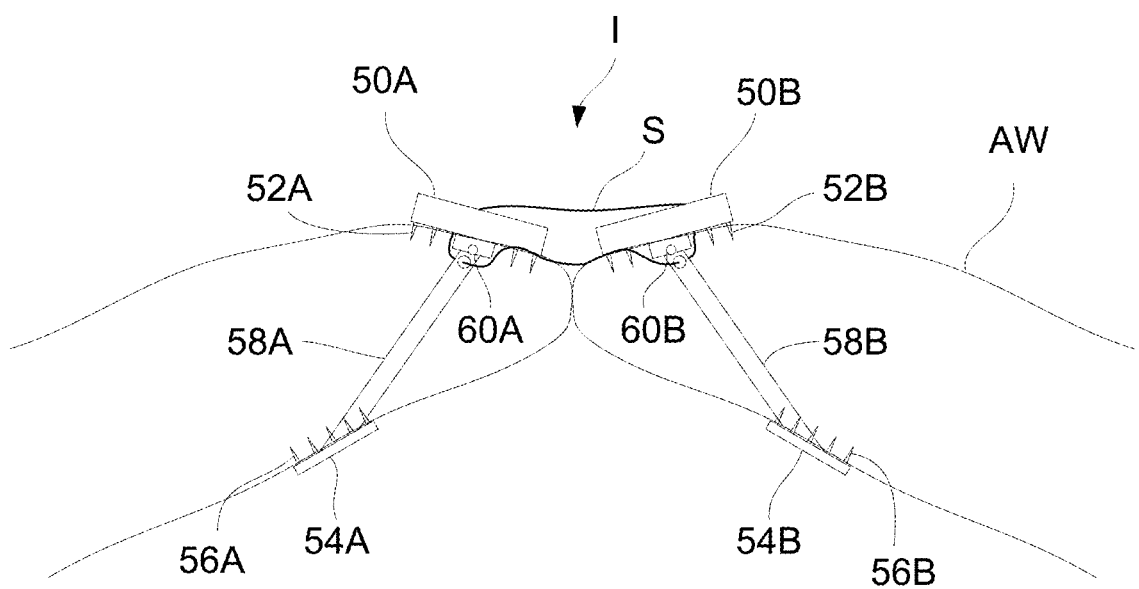
FIG. 6 shows a full thickness tissue anchor devoid of any intra-abdominal segment crossing the closure.

In another variation, the tissue anchor when deployed may comprise various mechanisms for holding a suture under tension between two devices, one on each side of the wound or incision, while the devices sandwich the abdominal wall between an inner and outer cap. FIG. 6 shows an example of a cross-sectional view of a device having a first tissue anchor having a distal anchor member 50A coupled to a proximal anchor member 54A via a connecting member 58A. The distal anchor member 50A may be configured to have one or more piercing elements such as tines 52A having a piercing distal tip which extend away from the platform of the distal anchor member 50A such that they project towards the proximal anchor member 54A. Similarly, the proximal anchor member 54A may have one or more tines 56A which extend away from the platform of the proximal anchor member 54A such that they project towards the distal anchor member 50A. The connecting member 58A may be pivotably coupled to the distal anchor member 50A and/or proximal anchor member 54A such that the anchor members 50A, 54A may pivot and angulate relative to one another and to the connecting member 58A. Alternatively, one or both of the anchor members 50A, 54A may be attached to the connecting member 58A at a fixed angle to facilitate securement to the underlying tissue.

In either case, during use the distal anchor member 50A may be positioned against a tissue surface (e.g., along the abdominal wall AW) near or in proximity to a first edge of a wound or incision I, as shown, such that the one or more tines 52A extend and penetrate posteriorly at least partially into the tissue such as the anterior rectus sheath, where medial abdominal wall tensile strength is greatest, or upon the skin surface. The connecting member 58A may extend entirely through the skin and/or fascia such that the proximal anchor member 54A is positioned along opposite thickness of tissue, such as the posterior rectus sheath where present above the arcuate line. The one or more tines 56A of the proximal tissue anchor 54A may extend and penetrate anteriorly at least partially into the tissue such that the intervening tissue thickness is sandwiched between the first and second tissue anchors 50A, 54A.

A second tissue anchor may be secured near or in proximity to a second edge of the wound or incision I, as shown, directly opposite to the first tissue anchor. Similarly, the second tissue anchor may have a distal anchor member 50A having one or more tines 52B which project posteriorly at least partially into the underlying tissue and a proximal anchor member 54B having one or more tines 56B which project anteriorly at least partially into the underlying tissue. The distal and proximal anchor members 50B, 54B may be coupled to one another via a connecting member 58B which extends through the thickness of the secured tissue region.

With the tissue anchors secured to the first and second edges of the wound or incision I, each of the distal anchor members 50A, 50B may be coupled to one another via a connecting member such as a suture S which may be secured to each of the tissue anchors, e.g., through one or more openings placed in the device to allow for suture passage. The suture S from one tissue anchor can connect to a tissue anchor, e.g., on the contralateral side, such that the suture S and tissue anchor assembly hold the edges in apposition while healing occurs.

Depending upon the length of the wound or incision I, any number of pairs of tissue anchors may be applied to the tissue to approximate and/or maintain closure of the wound such that each of the tissue anchors are applied along the edges of the wound or incision I adjacent to one another.

As described, the connecting members 58A, 58B that pass through the abdominal wall AW fascia and muscle may be angled or hinged relative to the respective anchor members to allow the medial forces of the suture S to align more in parallel with the anchoring component. This may help to reduce an anterior moment arm that would tend to apply all or most of the force at the anterior rectus sheath rather than across the entire abdominal wall thickness (anterior rectus sheath, rectus muscle, posterior rectus sheath where present). Additionally, each of the components of the tissue anchors may be fabricated from fully bioabsorbable materials such that the tissue anchors may be left in place to bioabsorb into the body over time. Alternatively, portions of the tissue anchors, such as the posterior anchor members 54A, 54B and/or connecting members 58A, 58B may be bioabsorbable while the distal anchor members 50A, 50B may be non-bioabsorbable. Once the wound or incision I has healed and adhered sufficiently, the distal anchor members 50A, 50B may be detached and removed from the tissue while the connecting members 58A, 58B and proximal anchor members 54A, 54B may be left in the body to become absorbed.

Figure 7:
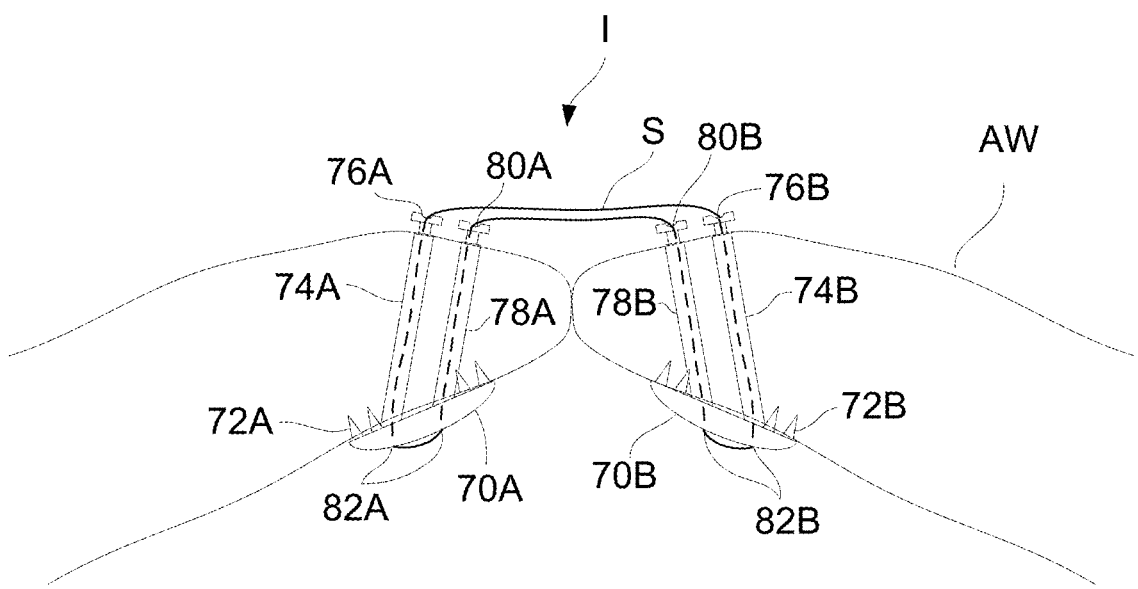
FIG. 7 shows anchors in which a loop of suture passes through two hollow columns before crossing the midline closure anterior to the abdominal wall.

Another variation is shown in the cross-sectional side view of FIG. 7 which shows a first tissue anchor having a posterior anchor member 70A with one or more tines 72A extending in a distal direction at least partially into the underlying tissue. One or more columns 74A, 78A each defining a lumen may project from the posterior anchor member 70A so that when the anchor member 70A is deployed against the tissue interior surface, each of the columns 74A, 78A may extend through the full thickness of fascia and/or skin tissue. As described above, the posterior anchor member 70A may have the one or more columns 74A, 78A extend at an angle relative to the anchor member 70A so that the columns 74A, 78A emerge from the tissue at an angle, as shown.

With a second tissue anchor secured to a second edge of the wound or incision I directly opposite to the first tissue anchor, a flexible couple member such as a suture S may be passed through each of the columns through a respective opening and through the length of the tissue anchor to join each of the tissue anchors. The suture S may be tightened to approximate and/or maintain the edges of the wound or incision I towards or directly against one another. As illustrated, the second tissue anchor may likewise have a posterior anchor member 70B with one or more tines 72B projecting into the contacted tissue. The one or more columns 74B, 78B may project from the anchor member 70B with a suture S passing between openings 80A and 80B, through the columns 78A and 78B, through or along each anchor member 70A and 70B, back through columns 74A and 74B, and through respective openings 76A and 76B.

Figure 8A:
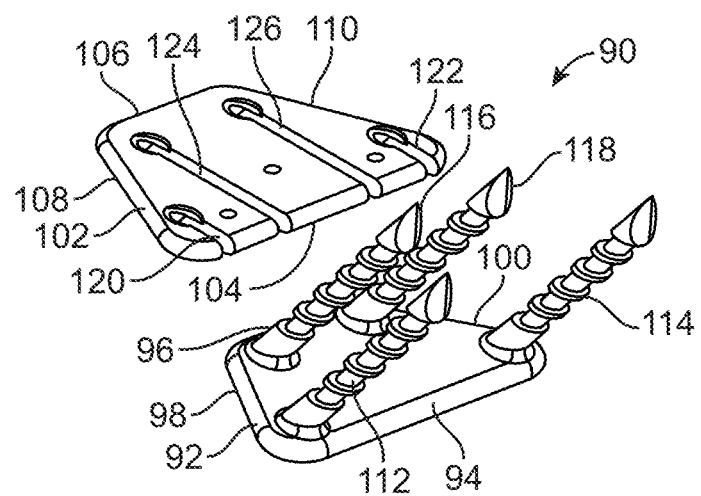
FIGS. 8A to 8C show a two-part anchor where a platform having tines may be positioned internal to the abdominal wall while a receiving member with corresponding openings may be positioned external to the abdominal wall.
Figure 8B:
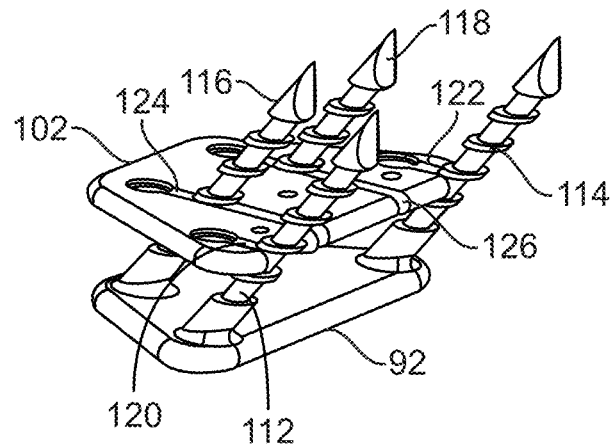
Figure 8C:
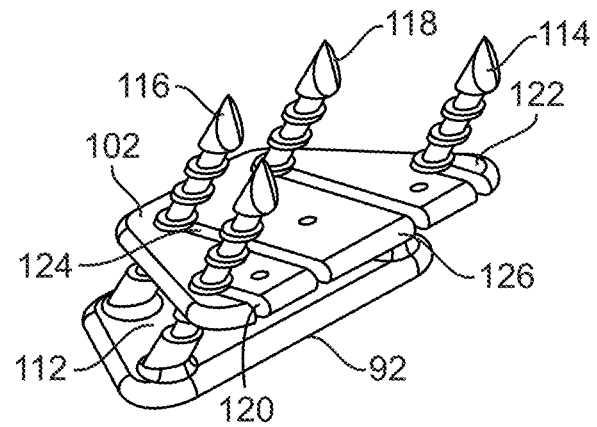

Turning now to yet another variation shown in the perspective views of FIGS. 8A to 8C, the tissue anchor 90 may be comprised of a first platform 94 having one or more piercing elements such as elongate columns or tines having a piercing tip which each project from the platform 94. In one variation, each of the tines may extend in parallel with one another or one or several of the tines may angled differently from one another. A second platform 102 may be separately attachable to each of the tines of the first platform 94 at various levels or distances such that a tissue region, such as the tissue near or in proximity to an edge of a wound or incision, may be sandwiched or secured between the first and second platform 92, 102.

The first platform 92 may be formed in various configurations (e.g., circular, ovular, triangular, rectangular, rhomboid, etc.) although the variation shown in FIG. 8A illustrates a platform 92 having a trapezoid-shaped configuration. The variation shown may have a first edge 94 (e.g., having a length of 20 mm to 50 mm) in parallel with a second edge 96 (e.g., having a length of 10 mm to 40 mm) which is relatively shorter in length than the first edge 94 and two side edges 98, 100 (e.g., each having a length of 10 mm to 50 mm) which are angled in opposite directions relative to one another and are relatively shorter than the first edge 94. The first platform 92 may have one or more tines which project from the surface of the platform 92 for attachment to a tissue region. In this example, two tines 112, 114 are illustrated projecting from the first platform 92 in proximity to the vertices between the first edge 94 and respective side edges 98, 100 and two additional tines 116, 118 are also illustrated projection from the first platform 92 in proximity to the vertices between the second edge 96 and respective side edges 98, 100. Each of the tines 112, 114, 116, 118 are shown to project parallel with one another each at an angle relative to the platform 92, as described in further detail below. The one or more tines may also range in length from the first platform of, e.g., 5 mm to 50 mm.

The second platform 102 is shown having a similar or same shape as the first platform 92 such that the first and second platforms 92, 102 may be oriented in the same direction. In other variations, the first and second platforms 92, 102 may each have a shape or configuration which is different from one another provided that the second platform 102 is still connectable to the first platform 92. In this example with the second platform 102 having the same configuration as the first platform 92, the second platform 102 may similarly have a first edge 104 and a second edge 106 in parallel where the second edge 106 is relatively shorter in length than the first edge 104. Two side edges 108, 110 may be angled in opposite directions relative to one another and are relatively shorter than the first edge 104.

The first edge 104 may further define a slot or channel which is located along the edge 104 corresponding to a position of the one or more tines extending from the first platform 92. Hence, a first slot 120 may be defined along the first edge 104 at a location corresponding to a first tine 112 and a second slot 122 may be defined along the first edge 104 at a location corresponding to a second tine 114. A third slot 124 may be defined along the first edge 104 at a location corresponding to a third tine 116 and a fourth slot 126 may be similarly defined along the first edge 104 at a location corresponding to a fourth tine 118. The first and second slots 120, 122 may extend along the second platform 102 into proximity towards each of the respective side edges 108, 110 while the third and fourth slots 124, 126 may extend along the second platform 102 into proximity towards the second edge 106, as shown. Additionally, each of the slots may correspond to the number of tines projecting from the first platform.

In use, the one or more tines 112, 114, 116, 118 of the first platform 92 may be pierced into a tissue region (such as the interior of the abdominal wall) and advanced entirely through the tissue thickness (e.g., fascia and skin or at least penetrate through the anterior rectus sheath, where tissue tensile strength is greatest) until the tissue abuts against the first platform 92. The second platform 102 may be positioned into proximity of the tines 112, 114, 116, 118 projecting through the tissue region and then slid to engage the first platform 92 by advancing the tines 112, 114, 116, 118 into and through a corresponding slot 120, 122, 124, 126, as shown in FIG. 8B. The second platform 102 may be engaged with the first platform 92 such that the two platforms 92, 102 are maintained in a parallel orientation relative to one another. Each of the tines 112, 114, 116, 118 may have predefined regions of reduced diameter over which the corresponding slots 120, 122, 124, 126 may selectively engage, as described in further detail below, such that the parallel orientation between the platforms 92, 102 is maintained. The second platform 102 may be advanced along the tines until the second platform 102 is fully engaged to the tines at the terminal ends of the slots, as shown in FIG. 8C.

The second platform 102 may be positioned along the tines 120, 122, 124, 126 such that the second platform 102 is positioned upon the tissue outer surface (such as the exterior of the abdominal wall or skin surface) and the tissue thickness is sandwiched or securely retained between each of the platforms 92, 102. Any length of the tines protruding beyond the second platform 102 may be cut, broken, or otherwise removed such that the tissue anchor maintains a low profile relative to the tissue surface.

The second tissue anchor may be secured in proximity to the edge of the wound or incision opposite to the first tissue anchor in the same manner, as described, such that the first and second tissue anchors may be attached or coupled to one another to approximate the tissue edges and maintain the edges in apposition during healing. The tissue anchors may be secured, e.g., via lengths of spanning suture or other materials attached through openings defined along the second platform 102, as described in further detail below. In other variations, other spanning structures may be used in place of sutures, e.g., elastic member, springs, coils, ratcheted device, spanning screw, adjustable staple or fixed staple, or other structure that crosses from a first tissue anchor to a second tissue anchor to cause and hold apposition of the abdominal wall tissues. With the tines along each of the tissue anchors angled towards one another (or angled towards the wound or incision), any forces imparted upon the tissue due to the approximation of the tissue anchors towards one another may be mitigated by a reduction in the moment arm of the tines upon the tissue thickness due to the tines angle relative to the first platform 92.

Moreover, with the tissue anchor secured through the tissue thickness, the entire tissue anchor may be fabricated from a bioabsorbable material, as described herein, such that the tissue anchor may be left in place in the body after the tissue has healed leaving the anchor to degrade and absorb over time thereby eliminating the need to remove the tissue anchor. Alternatively, the first platform 92 and tines may be fabricated from a bioabsorbable material while the second platform 102 may be fabricated from a non-bioabsorbable material, e.g., plastics, metals, alloys, etc. Once the tissue region has healed, the second platform 102 may be detached from the tines and then removed from the body leaving the first platform 92 and tines within the body to degrade and absorb.

Figure 9:
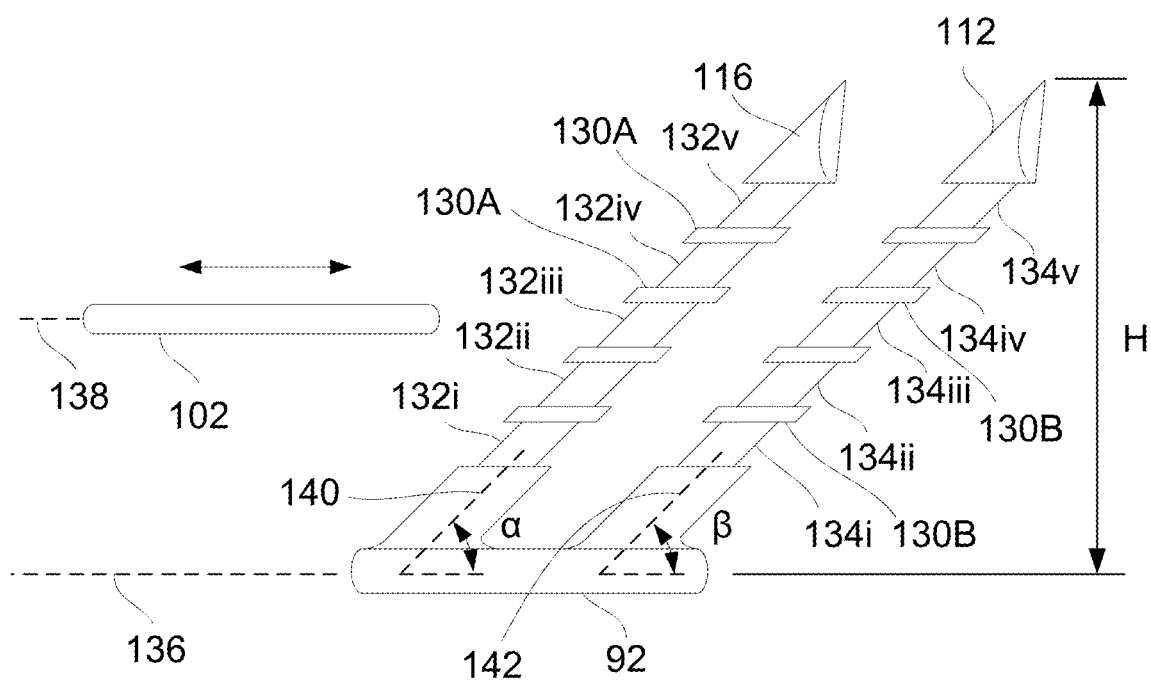
FIG. 9 shows a side view of two-part anchor to illustrate how the tines may be angled with respect to its base and receiving member.

FIG. 9 shows a side view of the first platform 92 and tines and second platform 102 to illustrate further details. As described above, the one or more tines may be configured to have one or more predefined regions of reduced diameter over which the corresponding slots 120, 122, 124, 126 of second platform 102 may selectively engage. Each of the tines may be formed to have these regions where the outer diameter of the respective tine is reduced to a second smaller diameter such. For instance, tine 112 may be formed with reduced regions 134$i$, 134$ii$, 134$iii$, 134$iv$, 134$v$ each separated by a shoulder 130B. Similarly, tine 116 may be formed with reduced regions 132$i$, 132$ii$, 132$iii$, 132$iv$, 132$v$ each separated by a shoulder 130A such that each reduced region may be formed to be correspondingly level relative to one another one between each tine. For instance, reduced region 132$i$ may be formed to be level with 134$i$, 132$ii$ may be formed to be level with 134$ii$, and so on. Moreover, the tines may be formed to have any number of reduced regions 132$n$, 134$n$ so long as each reduced region on each tine is level with one another. This enables the second platform 102 to be advanced and engaged to the tines at each reduced region such that the second platform 102 remains parallel with the first platform 92, e.g., the first plane 136 defined by first platform 92 is parallel with the second plane 138 defined by second platform 102.

As described above, each of the tines may be formed to project at an angle relative to the first platform 92. In this example, tines 116, 118 may define an angle α between a longitudinal axis 140 of the tine relative to the plane 136 of the first platform 92 and tines 112, 114 may define an angle β between a longitudinal axis 142 of the tine relative to the plane 136 of the first platform 92. While the angle α formed by tines 116, 118 may be the same or similar to the angle β formed by tines 112, 114 (e.g., ranging from 30 to 90 degrees), the angles between each of the tines may also vary from one another instead of being uniform. Additionally, the height H defined by the tines may also range from, e.g., 5 to 50 mm. The height of each of the tines may be uniform or they may be vary between each tine, if desired. In either case, the portion of the tines projecting beyond the second platform 102 when engaged to one another may be removed to maintain a low profile of the tissue anchor.

The first platform 92 is illustrated as having four tines; however, in other variations, the platform 92 may be configured to have fewer than four or more than four tines projecting from the platform 92. Furthermore, the first platform 92 may also optionally incorporate one or more secondary tines projecting from the first platform 92 between the tines. These secondary tines may be configured to be shorter in length than the primary tines for penetrating partially into the tissue, e.g., posterior rectus sheath, to provide for further anchoring of the first platform 92 relative to the tissue.

The tines may have any of a variety of cross-sectional geometries, e.g., circular, oval, rectilinear, etc. Furthermore, while the tines are shown as having an elongate shape with a piercing tip, the tines may be formed to be conic, parabolic, or other shapes. Moreover, the piercing tip of the tines can also be formed in various configurations, e.g., cutting, atraumatic, traumatic, multi-bevel, 'pencil' tip, etc.

Figure 10:
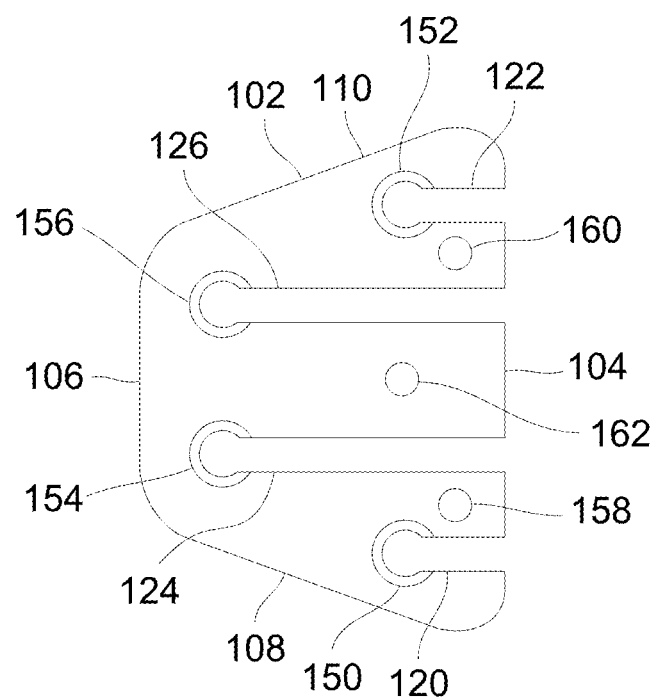
FIG. 10 shows a top view of a variation of the receiving member illustrating the receiving channels and openings.

The second platform 102 is also shown in FIG. 9 as having a smooth surface for presentation against the tissue surface. In other variations, one or more tines may also be formed to project from the second platform 102 for at least partial penetration into the underlying tissue. A top view of the second platform 102 is also shown in FIG. 10 which illustrates each of the slots 120, 122, 124, 126 for receiving a corresponding tine. The slots may extend from the first edge 104 and terminate in a respective receiving end 150, 152, 154, 156 which is configured to define a shoulder for receiving the tine in a secured manner. Furthermore, the second platform 102 is shown as having one or more openings 158, 160, 162 in proximity to the first edge 104 for receiving a coupling member such as a suture for attachment to another tissue anchor for approximating and/or maintaining a position of the tissue.

Additionally and/or alternatively, the tissue anchors may be secured in the tissue by use in combination with an absorbable or permanent mesh or a biologic sheet or insert. The one or more tines may be pierced into and through the mesh which may be placed against the tissue surface. The mesh or biologic component may sit at any plane in the abdominal wall anatomy while fixated by the tissue anchor.

An example of a first tissue anchor 90A attached to a second tissue anchor 90B is shown in the perspective view of FIG. 11 where the first tissue anchor 90A may be secured to a first edge in proximity to a wound or incision and where the second tissue anchor 90B may be secured to a second edge in proximity to the wound or incision and directly opposite to the first tissue anchor 90A. The secured tissue anchors 90A, 90B may be seen showing how the tines of each tissue anchor are positioned to be angled towards one another while the respective second platforms 102A, 102B are coupled to one another via sutures 174, 176. In this particular variation, the second platforms 102A, 102B may incorporate the tines 172A, 172B for attachment to the underlying tissue surface. Moreover, this variation may incorporate an additional securement platform or cap 170A, 170B which may be placed (either partially or over the entirety) upon the respective second platform 102A, 102B for engagement with the reduced portions along the tines. This third securement platform 170A, 170B may provide for additional anchoring of the second platform 102A, 102B to the tines.

Various tools may also be used to measure tension and avoid placing more than approximately, e.g., 32 mmHg of pressure resulting from static compression forces from the tissue anchor (e.g., first and/or second platforms), on the tissue thus preventing tissue necrosis or compromise. The static compression forces may accordingly be limited to a level which will typically not cause ischemic injury to the tissues.

The applications of the devices and methods discussed above are not limited to wound closure but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A tissue anchor apparatus, comprising:
    a first platform defining at least one anchoring member having a length extending from a surface of the first platform, the at least one anchoring member having a terminal piercing end;
    a second platform defining at least one elongated channel extending along a surface of the second platform from a peripheral edge of the second platform and terminated at a position of the at least one anchoring member when the at least one anchoring member is extended through the second platform,
    wherein an orientation of the second platform relative to the first platform is maintained by one or more shoulders defined along a length of the at least one anchoring member.

2. The apparatus of claim 1 further comprising a retaining platform defining at least one opening which correspond to a position of the at least one anchoring member.

3. The assembly of claim 1 further comprising one or more securing elements attachable to a portion of the second platform for securement to an additional tissue anchor positioned opposite to the tissue anchor.

4. The assembly of claim 3 wherein the one or more securing elements comprise a length of suture or biasing element.

5. The assembly of claim 1 wherein the first platform defines a trapezoidal configuration having four anchoring members.

6. The assembly of claim 1 wherein each anchoring member extends from the surface in parallel with one another.

7. The assembly of claim 1 wherein each anchoring member is angled relative to the first platform.

8. The assembly of claim 1 wherein the one or more shoulders are defined by regions of reduced diameter along the length of the at least one anchoring member.

9. The assembly of claim 1 the second platform further comprises at least one secondary anchoring member extending from a surface of the platform opposite to the surface of the first platform.

10. The assembly of claim 9 wherein the at least one secondary anchoring member comprises tines each having a length which is less than the at least one anchoring member from the first platform.

11. The assembly of claim 1 wherein the first platform and second platform have a parallel orientation relative to one another.

12. The assembly of claim 1 wherein each of the at least one anchoring member have a uniform height relative to the surface of the first platform.

13. The assembly of claim 1 wherein a portion of the at least one anchoring member extending beyond the second platform when engaged to the first platform is removable.

14. The assembly of claim 1 wherein the first platform is configured to be bioabsorbable.

15. The assembly of claim 1 wherein the second platform is configured to be bioabsorbable.

16. The assembly of claim 1 further comprising a third platform configured to secure the second platform to the at least one or more anchoring member.

17. The assembly of claim 1 wherein a position of the at least one elongated channel along the edge is aligned with the at least one anchoring member.

18. A tissue anchor apparatus, comprising:
    a first platform defining at least one anchoring member having a length extending from a surface of the first platform, the at least one anchoring member having a terminal piercing end and defining an engagement region along the length;
    a second platform defining an opening for correspondingly receiving the at least one anchoring member and defining at least one elongated channel extending along a surface of the second platform from a peripheral edge of the second platform such that the at least one channel is aligned with and terminated at a position of the at least one anchoring member when the at least one anchoring member is extended through the second platform; and
    a third platform configured to be positioned upon the second platform when engaged upon the at least one anchoring member such that the second platform is secured to the at least one anchoring member along the engagement region.

19. The apparatus of claim 18 further comprising additional anchoring members extending from the surface of the first platform.

20. The apparatus of claim 18 wherein the second platform further defines an attachment region.

21. The apparatus of claim 20 further comprising a length of suture or a biasing element for coupling to the attachment region.

22. The apparatus of claim 18 wherein the second platform is relatively smaller in diameter than the first platform.

23. The apparatus of claim 18 wherein the second platform is relatively larger in diameter than the first platform.

24. The apparatus of claim 18 wherein the first platform and second platform have a parallel orientation relative to one another.

25. The apparatus of claim 18 wherein a portion of the at least one anchoring member extending beyond the second platform when engaged to the first platform is removable.

26. The apparatus of claim 18 wherein the first platform is configured to be bioabsorbable.

27. The apparatus of claim 18 wherein the second platform is configured to be bioabsorbable.

28. The apparatus of claim 18 wherein the third platform is configured to be bioabsorbable.

29. The apparatus of claim 18 wherein the second platform is secured to the at least one anchoring member along the engagement region such that an orientation of the second platform is maintained relative to the first platform.

* * * * *